(12) United States Patent
Fink et al.

(10) Patent No.: US 7,982,033 B2
(45) Date of Patent: *Jul. 19, 2011

(54) PYRROLOTRIAZINE KINASE INHIBITORS

(75) Inventors: Brian E. Fink, West Windsor, NJ (US); Ping Chen, Franklin Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/447,751

(22) PCT Filed: Nov. 2, 2007

(86) PCT No.: PCT/US2007/083436
§ 371 (c)(1),
(2), (4) Date: Oct. 2, 2009

(87) PCT Pub. No.: WO2008/057994
PCT Pub. Date: May 15, 2008

(65) Prior Publication Data
US 2010/0081662 A1    Apr. 1, 2010

Related U.S. Application Data

(60) Provisional application No. 60/864,175, filed on Nov. 3, 2006.

(51) Int. Cl.
C07D 487/04 (2006.01)
A61K 31/53 (2006.01)
A61P 35/00 (2006.01)

(52) U.S. Cl. ........................................ 544/183; 514/243
(58) Field of Classification Search .................. 544/183; 514/243
See application file for complete search history.

(56) References Cited

U.S. PATENT DOCUMENTS

| 6,670,357 B2 | 12/2003 | Leftheris et al. |
| 6,951,859 B2 | 10/2005 | Bhide et al. |
| 6,982,265 B1 | 1/2006 | Hunt et al. |
| 7,160,883 B2 | 1/2007 | Dyckman et al. |
| 7,531,539 B2* | 5/2009 | Fink et al. ............... 514/243 |
| 7,605,160 B2* | 10/2009 | Fink et al. ............... 514/243 |
| 2008/0045496 A1 | 2/2008 | Fink et al. |
| 2008/0058337 A1 | 3/2008 | Fink et al. |

FOREIGN PATENT DOCUMENTS

| WO | WO 00/71129 | 11/2000 |
| WO | WO 02/40486 | 5/2002 |
| WO | WO 03/090912 | 11/2003 |
| WO | WO 2004/013145 | 2/2004 |
| WO | WO 2008/131050 | 10/2008 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p4.*
Dermer et al., Bio/Technology, 1994, 12:320.*
Powell et al., British Journal of Dermatology, 141: 802-810, 1999.*
Cohen et al., Current Opinion in Chemical Biology, 3,459-465, 1999.*
Golub et al., Science, 286, 531-537, 1999.*
Mass, R. D., Int. J. Radiation Oncology Bio. Phys.vol. 58(3): 932-940, 2004.*
Fabbro et al. Pharmacology & Therapeutics 93, 79-98, 2002.*

* cited by examiner

Primary Examiner — Venkataraman Balasubramanian
(74) Attorney, Agent, or Firm — Elliott Korsen

(57) ABSTRACT

The invention provides compounds of formula I

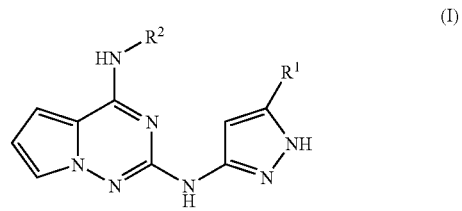

and pharmaceutically acceptable salts thereof.
The formula I compounds inhibit tyrosine kinase activity of Trk receptors such as TrkA, TrkB, TrkC or Flt-3 thereby making them useful as anticancer agents.

4 Claims, No Drawings

PYRROLOTRIAZINE KINASE INHIBITORS

FIELD OF THE INVENTION

This invention relates to novel compounds that are useful as anti-cancer agents. This invention also relates to a method of using the compounds in the treatment of proliferative diseases, such as cancer, and to pharmaceutical compositions containing the compounds.

BACKGROUND OF THE INVENTION

Tropomysosin Related Kinases (Trk) are a family of receptor tyrosine kinases composed of three family members, TrkA, TrkB and TrkC. The Trks bind with high affinity to, and mediate the signal transduction induced by the Neurotrophin family of ligands whose prototype members are Nerve Growth Factor (NGF), Brain-Derived Neurotrophic Factor (BDNF) and Neurotrophin-3, -4 and -5 (NT-3, NT-4 and NT-5). In addition, a co-receptor lacking enzymatic activity, p75, has been identified which binds all neurotrophins (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. In addition to these developmental consequences of Trk signaling, the subversion of this receptor and its signaling pathway in certain malignancies has also been documented. Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. In addition, profound or significantly attenuated reduction of bone pain caused by prostate cancer metastasis has recently been achieved by utilization of an anti-NGF antibody. Overall, the oncogenic properties of Trk signaling in multiple tumor types makes the modulation of the Trk receptor signaling a potentially attractive therapeutic intervention point in different malignancies.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. In general, RTKs are activated by ligand-induced oligomerization and tyrosine autophosphorylation of specific intracellular substrates such as PLCγ; PI3 kinase, ras, and raf/MEK/Erk1. Tyrosine kinase activity is an absolute requirement for signal transduction through this class of receptor.

The Trk family of RTKs is frequently expressed in lung, breast, pancreatic and prostate cancers as well as in certain type of acute myelogenous leukemia and congenital fibrosarcoma. The tyrosine kinase activity of Trk is believed to promote the unregulated activation of cell proliferation machinery. It is believed that inhibitors of either TrkA, TrkB, or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies.

DETAILED DESCRIPTION OF THE INVENTION

The invention provides for compounds of formula I, pharmaceutical compositions employing such compounds and for methods of using such compounds.

In accordance with the invention, there are disclosed compounds of formula I

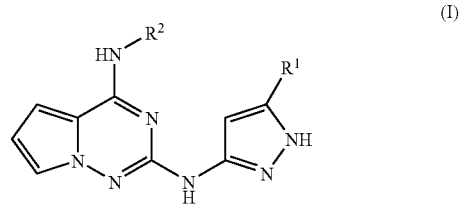

(I)

wherein the symbols have the following meanings and, for each occurrence, are independently selected:

$R^1$ is hydrogen, alkyl, substituted alkyl, cycloalkyl, substituted cycloalkyl, aryl or substituted aryl;

$R^2$ is alkyl, substituted alkyl, cycloalkyl, substituted cycloalkyl, aryl, substituted aryl, heterocyclyl, substituted heterocyclyl, cycloalkylalkyl, substituted cycloalkylalkyl, arylalkyl, substituted arylalkyl, heterocyclylalkyl, substituted heterocyclylalkyl, —$(CH_2)_n$-substituted alkyl, —$(CH_2)_n$-aryl, —$(CH_2)_n$-substituted aryl, —$(CH_2)_n$-substituted heteroaryl, —$(CH_2)_n$—OH, —$(CH_2)_n$—$NH_2$, —$(CH_2)_n$—S-alkyl or —$SO_2$ alkyl, two of which may be attached to the same ring carbon;

n is 0, 1, 2, 3 or 4;

or a pharmaceutically acceptable salt or stereoisomer thereof.

In another embodiment, the invention comprises a compound of formula II wherein

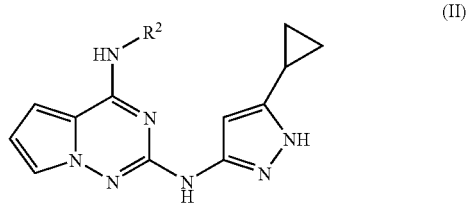

(II)

wherein

R² is alkyl, substituted alkyl, cycloalkyl, substituted cycloalkyl, aryl, substituted aryl, heterocyclyl, substituted heterocyclyl, cycloalkylalkyl, substituted cycloalkylalkyl, arylalkyl, substituted arylalkyl, heterocyclylalkyl, substituted heterocyclylalkyl, —(CH$_2$)$_n$-substituted alkyl, —(CH$_2$)$_n$-aryl, —(CH$_2$)$_n$-substituted aryl, —(CH$_2$)$_n$-substituted heteroaryl, —(CH$_2$)$_n$—OH, —(CH$_2$)$_n$—NH$_2$, —(CH$_2$)$_n$—S-alkyl or —SO$_2$ alkyl, two of which may be attached to the same ring carbon atom; and n is 0, 1, 2, 3 or 4;

or a pharmaceutically acceptable salt or stereoisomer thereof.

Compounds of the invention include the following

N²-(5-cyclopropyl-1H-pyrazol-3-yl)-N⁴-((1S)-1-(4-fluorophenyl)ethyl)pyrrolo[2,1-f][1,2,4]triazine-2,4-diamine, N²-(5-cyclopropyl-1H-pyrazol-3-yl)-N⁴-((1S)-1-methylpentyl)pyrrolo[2,1-f][1,2,4]triazine-2,4-diamine, N⁴-(1-benzyl-3-pyrrolidinyl)-N²-(5-methyl-1H-pyrazol-3-yl)pyrrolo[2,1-f][1,2,4]triazine-2,4-diamine, N⁴-(3-cyclopropyl-1H-pyrazol-5-yl)-N²-((1S)-1-phenylethyl)pyrrolo[2,1-f][1,2,4]triazine-2,4-diamine, N⁴-(3-cyclopropyl-1H-pyrazol-5-yl)-N²-((1R)-1-phenylethyl)pyrrolo[2,1-f][1,2,4]triazine-2,4-diamine, N⁴-((1S)-1-(4-fluorophenyl)ethyl)-N²-(5-methyl-1H-pyrazol-3-yl)pyrrolo[2,1-f][1,2,4]triazine-2,4-diamine, N⁴-cycloheptyl-N²-(5-cyclopropyl-1H-pyrazol-3-yl)pyrrolo[2,1-f][1,2,4]triazine-2,4-diamine, N⁴-(cyclohexylmethyl)-N²-(5-cyclopropyl-1H-pyrazol-3-yl)pyrrolo[2,1-f][1,2,4]triazine-2,4-diamine, N⁴-((1S)-1-cyclohexylethyl)-N²-(5-cyclopropyl-1H-pyrazol-3-yl)pyrrolo[2,1-f][1,2,4]triazine-2,4-diamine, or a pharmaceutically acceptable salt thereof.

The following are definitions of terms that may be used in the specification. The initial definition provided for a group or term herein applies to that group or term throughout the specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., R³) occurs more than one time in any constituent or formula for a compound, its definition at each occurrence is independent of its definition at every other occurrence. Thus, for example, if a group is shown to be substituted with 0-2 R³, then said group may optionally be substituted with up to two R³ groups and R³ at each occurrence is selected independently from the definition of R³. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, arylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamino, sulfonic acid, alkylsulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzopyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to —$R^k$S(=O)$_2$$R^k$, wherein $R^k$ is an alkyl or substituted alkyl.

The term "oxo" refers to the divalent radical =O.

The term "carbamate" refers to the group —OC(=O)NH$_2$.

The term "amide" refers to the group —C(=O)NH$_2$.

The term "sulfonamide" refers to the group —SO$_2$NH$_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —C(=O)N$R^m$$R^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group —SO$_2$NR$^o$R$^p$ wherein R$^o$ and R$^p$ are independently selected from alkyl, substituted alkyl, alkenyl, substituted alkenyl, cycloalkyl, and substituted cycloalkyl, provided at least one of R$^o$ or R$^p$ is a substituted moiety.

A substituted carbamate, for example, refers to the group —OC(=O)NR$^q$R$^r$ wherein R$^q$ and R$^r$ are independently selected from alkyl, substituted alkyl, alkenyl, substituted alkenyl, cycloalkyl, and substituted cycloalkyl, provided at least one of R$^q$ or R$^r$ is a substituted moiety.

The term "ureido" refers to the group —NHC(=O)NH$_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "alkylthio" refers to the group —SR$^s$ where R$^s$ is an alkyl, substituted alkyl, cycloalkyl, or substituted cycloalkyl.

The term "thioalkyl" refers to the group —R$^t$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —OC(=O)NHR$^x$, and/or —OC(=O)NR$^y$R$^z$, wherein R$^y$ and R$^z$ are independently selected from alkyl and substituted alkyl.

The group —NR$^6$(C=O)R$^9$ refers to a group where R$^6$ is selected from hydrogen, lower alkyl and substituted lower alkyl, and R$^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the invention may be delivered in prodrug form. Thus, the invention is intended to cover prodrugs of the claimed compounds, methods of delivering the same and compositions containing the same. "Prodrugs" are intended to include any covalently bonded carriers that release an active parent drug of the invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, p. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that these recited compounds do not contain a N-halo, S(O)$_2$H, or S(O)H group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The invention further includes compositions comprising one or more compounds of the invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

UTILITY

The invention is based on the discovery that certain pyrrolotriazines are inhibitors of protein kinases. More specifically, pyrrolotriazines such as those described in this invention inhibit the protein tyrosine kinase activity of members of the TRK family of receptors. These inhibitors will be useful in the treatment of proliferative diseases that are dependent on signaling by one or more of these receptors. Such diseases include solid tumors of the pancreatic, prostate, lung, head and neck, breast, colon, ovary, as well as other tumor types including multiple myeloma, melanoma, neuroblastoma, glioblastoma and acute myelogenous leukemia. The invention also relates to a pharmaceutical composition of compound of formula I, or a pharmaceutically acceptable salt or stereoisomer thereof, and a pharmaceutically acceptable carrier in the treatment of cancer in a mammal. In particular, said pharmaceutical composition is expected to inhibit the growth and/or metastasis of those primary and recurrent solid tumors which are associated with TrkA, TrkB, TrkC, Flt-3 (Fms-like kinase-3) and Tie-2, especially those tumors which are significantly dependent on TrkA, TrkB, TrkC, Flt-3, Tie-2 for their growth and spread, including for example, cancers of the thyroid, breast, colon, pancreas, or a variety of tumor types including multiple myeloma, melanoma, neuroblastoma and glioblastoma.

Thus according to a further aspect of the invention there is provided the use of a compound of formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined hereinbefore.

By virtue of their ability to inhibit TrkA, TrkB, Trk C, Flt-3 and Tie-2 kinases, compounds of the invention can be used for the treatment of proliferative diseases, including cancer. The TrkA, TrkB and TrkC receptor kinases have been shown to be expressed and activated in tumors including thyroid, breast, colon, and elevated Trk receptors and corresponding ligands have also been reported in a variety of tumor types including multiple myeloma, melanoma, pancreatic carcinoma, neuroblastoma and glioblastoma. It is therefore expected that inhibitors of the TrkA, TrkB and TrkC kinases will have efficacy in the treatment of tumors that depend on signaling from either or both of the receptors. These compounds are expected to have efficacy either as single agent or in combination (simultaneous or sequentially) with other chemotherapeutic agents such as Taxol®, adriamycin, and cisplatin.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib (Sprycel®), Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-deacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabine, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in the treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fme-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

BIOLOGICAL ASSAYS

TrkA

The ability of compounds of the invention to inhibit tyrosine kinase activity of TrkA may be measured using a recombinant enzyme in an assay that measures the ability of compounds to inhibit the phosphorylation of the exogenous substrate, polyGluTyr (PGT, 4:1). The kinase domain of the human TrkA receptor is expressed in Sf9 insect cells as a histidine (His)-fusion protein using a baculovirus expression system. The protein is purified from the lysates of these cells using an Ni-NTA affinity column. After the recombinant enzyme is purified, it is activated by incubation with cold ATP. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol). After a 1 hour incubation at 30° C., the reaction is terminated with 10% TCA and incubated at 4° C. for 1 hour. The reaction is filtered onto a Unifilter® GF/C™ filter plate that has been presoaked with 0.1M NaPyrophosphate. Microscint-20 is then added to the dried filter plate and the captured $^{33}$P-phosphorylated PGT is quantitated on a microscintillation plate counter (TopCount·NXT™). Inhibition of the kinase enzymatic activity by the test compound is detected by a reduction in scintillation, and the concentration of compound that is required to inhibit the signal by 50% is reported as the $IC_{50}$ value for the test compound.

TrkB

The ability of compounds of the invention to inhibit tyrosine kinase activity of TrkB may be measured using a recombinant enzyme in an assay that measures the ability of compounds to inhibit the phosphorylation of the exogenous substrate, polyGluTyr (PGT, 4:1). The kinase domain of the human TrkB receptor (amino acids 526-838) is expressed in insect cells as a histidine (His)-fusion protein and is commercially available from Invitrogen™. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol). After a 1 hour incubation at 30° C., the reaction is terminated with 10% TCA and incubated at 4° C. for 1 hour. The reaction is filtered onto a Unifilter® GF/C™ filter plate that has been pre-soaked with 0.1M NaPyrophosphate. Microscint-20 is then added to the dried filter plate and the captured $^{33}$P-phosphorylated PGT is quantitated on a microscintillation plate counter (TopCount·NXT™). Inhibition of the kinase enzymatic activity by the test compound is detected by a reduction in scintillation, and the concentration of compound that is required to inhibit the signal by 50% is reported as the $IC_{50}$ value for the test compound.

The instant compounds inhibit TrkA and TrkB with $IC_{50}$ values between 0.001 to 10 μM. Preferred compounds have $IC_{50}$ values between 0.001-2.5 μM. More preferred compounds have $IC_{50}$ values between 0.001-0.5 μM. Most preferred compounds have $IC_{50}$ values between 0.001-0.1 μM. Representative compounds are listed in following table.

| Ex. No. | TrkA $IC_{50}$ (μM) | TrkB $IC_{50}$ (μM) |
|---------|---------------------|---------------------|
| 1       | 0.0003              | 0.0008              |
| 21      | 0.0005              | 0.002               |
| 24      | 0.036               | 0.064               |
| 32      | 0.002               | 0.003               |

Methods of Preparation

Certain compounds of formula I may generally be prepared according to the following schemes and the knowledge of one skilled in the art.

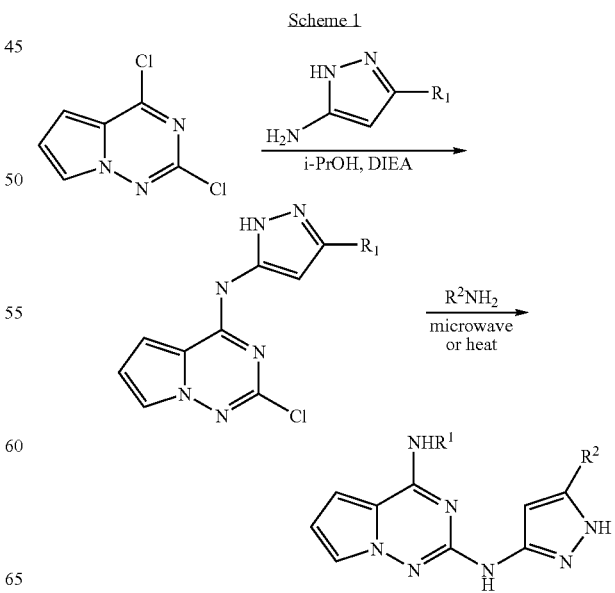

EXAMPLE 1

N²-(5-cyclopropyl-1H-pyrazol-3-yl)-N⁴-((1S)-1-(4-fluorophenyl)ethyl)pyrrolo[2,1-f][1,2,4]triazine-2,4-diamine

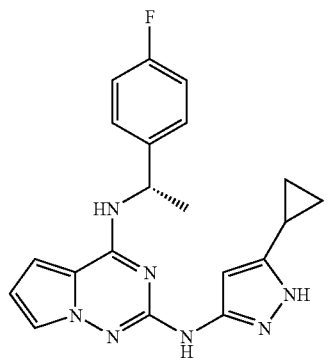

1A. Preparation of 2-chloro-N-(3-cyclopropyl-1H-pyrazol-5-yl)pyrrolo[1,2-f][1,2,4]triazin-4-amine

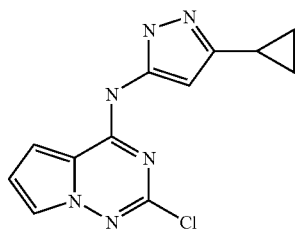

A solution of 2,4-dichloropyrrolo[1,2-f][1,2,4]triazine (1.5 g, 5.3 mmol) in i-PrOH (15 mL) was treated with 3-cyclopropyl-1H-pyrazol-5-amine (657 mg, 5.3 mmol) and DIEA (0.92 mL, 5.3 mmol). The reaction was stirred overnight at ambient temperature and then filtered. The filter cake was washed with cold i-PrOH and dried under vacuum to afford 1A as a solid (1.3 g, 90%). HPLC $t_R$=3.301 min (YMC S5 Combiscreen ODS 4.6×50 mm, 10-90% aqueous methanol containing 0.2% $H_3PO_4$, 4 min gradient, monitored at 220 nm). [M+H]⁺=275.37.

1B. Preparation of N²-(5-cyclopropyl-1H-pyrazol-3-yl)-N⁴-((1S)-1-(4-fluorophenyl)ethyl)pyrrolo[2,1-f][1,2,4]triazine-2,4-diamine

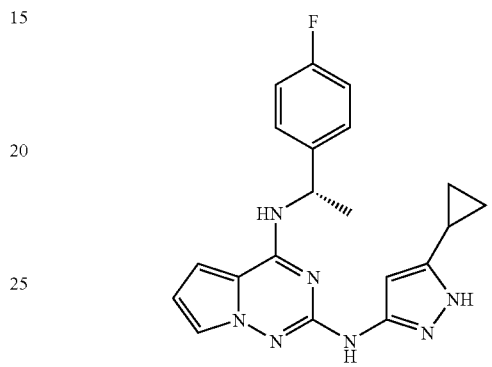

A mixture of 2-chloro-N-(3-cyclopropyl-1H-pyrazol-5-yl)pyrrolo[1,2-f][1,2,4]triazin-4-amine 1A (200 mg, 0.74 mmol) and (S)-1-(4-fluorophenyl)ethanamine (0.5 mL) was heated in a microwave safe tube (10 mL) at 120° C. for 50 minutes using 300 W continuous power. The reaction was diluted with MeOH (1.5 mL) and purified by preparative reversed-phase HPLC to afford the title compound as a solid (220 mg, 40%). HPLC $t_R$=3.093 min (YMC S5 ODS 4.6×50 mm, 10-90% aqueous methanol containing 0.2% $H_3PO_4$, 4 min gradient, monitored at 220 nm). [M+H+]=378.36.

The following compounds in Table 1 have been synthesized utilizing the procedures described in Example 1.

TABLE 1

| Ex. # | R¹ | R² | Compound name | [M + H] | HPLC Ret Time (min) |
|---|---|---|---|---|---|
| 2 | cyclopropyl-CH< | phenyl-CH₂-NH- | N⁴-benzyl-N²-(5-cyclopropyl-1H-pyrazol-3-yl)pyrrolo[2,1-f][1,2,4]triazine-2-diamine | 346.35 | 2.988ᵃ |

TABLE 1-continued

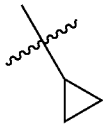

| Ex. # | R¹ | R² | Compound name | [M + H] | HPLC Ret Time (min) |
|---|---|---|---|---|---|
| 3 |  | 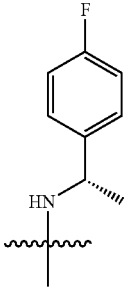 | (2S)-2-((2-((5-cyclopropyl-1H-pyrazol-3-yl)amino)pyrrolo[2,1-f][1,2,4]triazin-4-yl-yl)amino)-2-phenylethanol | 376.38 | 2.69[b] |
| 4 | Me | 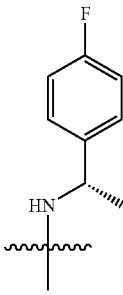 | N⁴-((1S)-1-(4-fluorophenyl)ethyl)-N²-(5-methyl-1H-pyrazol-3-yl)pyrrolo[2,1-f][1,2,4]triazine-2,4-diamine | 352.38 | 2.755[b] |
| 5 | tBu | 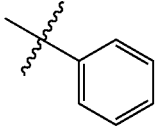 | N²-(5-tert-butyl-1H-pyrazol-3-yl)-N⁴-((1S)-1-(4-fluorophenyl)ethyl)pyrrolo[2,1-f][1,2,4]trazine-2,4-diamine | 394.39 | 3.19[b] |
| 6 | 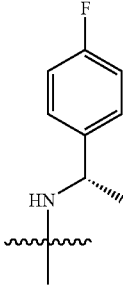 | 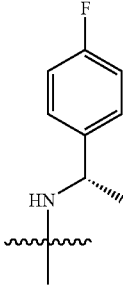 | N⁴-((1S)-1-(4-fluorophenyl)ethyl)-N²-(5-phenyl-1H-pyrazol-3-yl)pyrrolo[2,1-f][1,2,4]triazine-2,4-diamine | 414.35 | 3.308[b] |

TABLE 1-continued

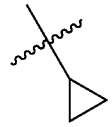

| Ex. # | R¹ | R² | Compound name | [M + H] | HPLC Ret Time (min) |
|---|---|---|---|---|---|
| 7 | 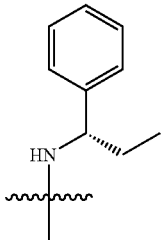 | 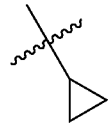 | $N^2$-(5-cyclopropyl-1H-pyrazol-3-yl)-$N^4$-((1S)-1-phenylpropyl)pyrrolo[2,1-f][1,2,4]triazine-2,4-diamine | 374.4 | 3.303[c] |
| 8 | 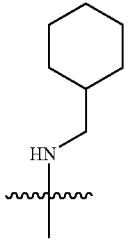 | 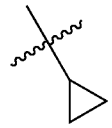 | $N^4$-(cyclohexylmethyl)-$N^2$-(5-cyclopropyl-1H-pyrazol-3-yl)pyrrolo[2,1-f][1,2,4]triazine-2,4-diamine | 352.41 | 3.20[b] |
| 9 | 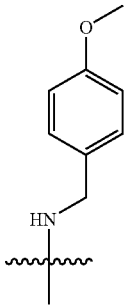 | 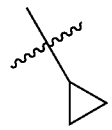 | $N^2$-(5-cyclopropyl-1H-pyrazol-3-yl)-$N^4$-(4-methoxybenzyl)pyrrolo[2,1-f][1,2,4]triazine-2,4-diamine | 376.33 | 2.955[a] |
| 10 | 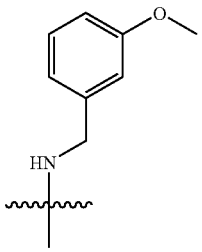 | 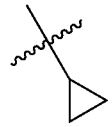 | $N^2$-(5-cyclopropyl-1H-pyrazol-3-yl)-$N^4$-(3-methoxybenzyl)pyrrolo[2,1-f][1,2,4]triazine-2,4-diamine | 376.35 | 2.960[a] |
| 11 | 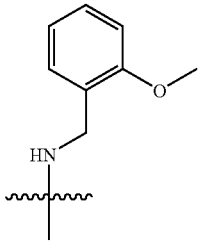 | | $N^2$-(5-cyclopropyl-1H-pyrazol-3-yl)-$N^4$-(2-methoxybenzyl)pyrrolo[2,1-f][1,2,4]triazine-2,4-diamine | 376.34 | 3.061[a] |

TABLE 1-continued

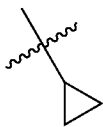

| Ex. # | R¹ | R² | Compound name | [M + H] | HPLC Ret Time (min) |
|---|---|---|---|---|---|
| 12 | 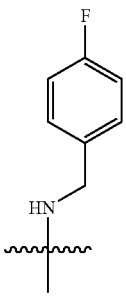 | 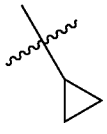 | $N^2$-(5-cyclopropyl-1H-pyrazol-3-yl)-$N^4$-(4-fluorobenzyl)pyrrolo[2,1-f][1,2,4]triazine-2,4-diamine | 364.33 | 3.041[a] |
| 13 | 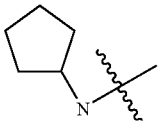 | 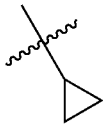 | $N^4$-cyclopentyl-$N^2$-(5-cyclopropyl-1H-pyrazol-3-yl)pyrrolo[2,1-f][1,2,4]triazine-2,4-diamine | 324.37 | 2.818[b] |
| 14 | 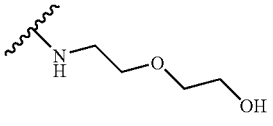 | 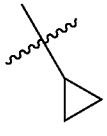 | 2-(2-((2-((5-cyclopropyl-1H-pyrazol-3-yl)amino)pyrrolo[2,1-f][1,2,4]triazin-4-yl)amino)ethoxy)ethanol | 344.37 | 2.082[b] |
| 15 | 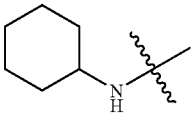 | 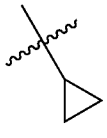 | $N^4$-cyclohexyl-$N^2$-(5-cyclopropyl-1H-pyrazol-3-yl)pyrrolo[2,1-f][1,2,4]triazine-2,4-diamine | 338.37 | 3.233[b] |
| 16 | 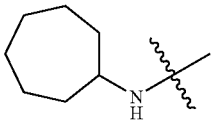 | 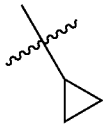 | $N^4$-cycloheptyl-$N^2$-(5-cyclopropyl-1H-pyrazol-3-yl)pyrrolo[2,1-f][1,2,4]triazine-2,4-diamine | 352.4 | 3.171[b] |
| 17 | 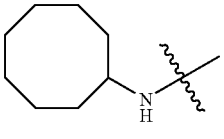 | 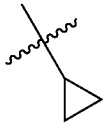 | $N^4$-cyclooctyl-$N^2$-(5-cyclopropyl-1H-pyrazol-3-yl)pyrrolo[2,1-f][1,2,4]triazine-2,4-diamine | 366.43 | 3.331[b] |
| 18 | 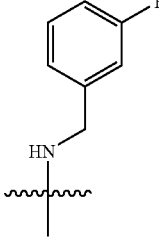 | | $N^2$-(5-cyclopropyl-1H-pyrazol-3-yl)-$N^4$-(3-fluorobenzyl)pyrrolo[2,1-f][1,2,4]triazine-2,4-diamine | 364.38 | 3.065[a] |

TABLE 1-continued

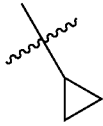

| Ex. # | R¹ | R² | Compound name | [M + H] | HPLC Ret Time (min) |
|---|---|---|---|---|---|
| 19 | 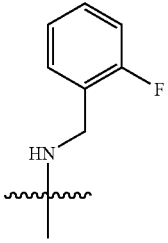 | 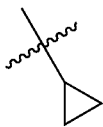 | $N^2$-(5-cyclopropyl-1H-pyrazol-3-yl)-$N^4$-(2-fluorobenzyl)pyrrolo[2,1-f][1,2,4]triazine-2,4-diamine | 364.37 | 3.055[a] |
| 20 | 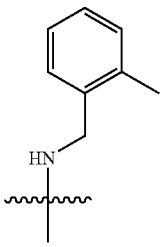 | 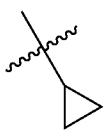 | $N^2$-(5-cyclopropyl-1H-pyrazol-3-yl)-$N^4$-(2-methylbenzyl)pyrrolo[2,1-f][1,2,4]triazine-2,4-diamine | 360.37 | 3.133[a] |
| 21 | 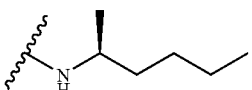 | 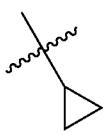 | $N^2$-(5-cyclopropyl-1H-pyrazol-3-yl)-$N^4$-((1S)-1-methylpentyl)pyrrolo[2,1-f][1,2,4]triazine-2,4-diamine | 340.41 | 3.131[b] |
| 22 | 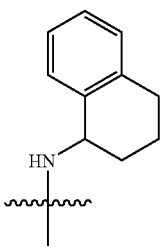 | 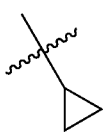 | $N^2$-(5-cyclopropyl-1H-pyrazol-3-yl)-$N^4$-(1,2,3,4-tetrahydro-1-naphthalenyl)pyrrolo[2,1-f][1,2,4]triazine-2,4-diamine | 386.37 | 3.156[b] |
| 23 | 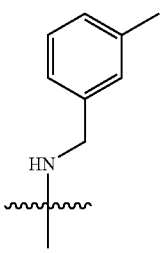 | 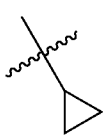 | $N^2$-(5-cyclopropyl-1H-pyrazol-3-yl)-$N^4$-(3-methylbenzyl)pyrrolo[2,1-f][1,2,4]triazine-2,4-diamine | 360.37 | 3.148[a] |
| 24 | 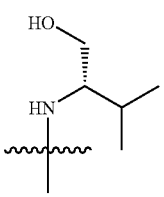 | | (2S)-2-((2-((5-cyclopropyl-1H-pyrazol-3-yl)amino)pyrrolo[2,1-f][1,2,4]triazin-4-yl)amino)-3-methyl-1-butanol | 342.42 | 2.618[b] |

TABLE 1-continued

| Ex. # | R¹ | R² | Compound name | [M + H] | HPLC Ret Time (min) |
|---|---|---|---|---|---|
| 25 | cyclopropyl | 4-methylbenzyl-NH-CH₂- | N²-(5-cyclopropyl-1H-pyrazol-3-yl)-N⁴-(4-methylbenzyl)pyrrolo[2,1-f][1,2,4]triazine-2,4-diamine | 360.39 | 3.143$^a$ |
| 26 | cyclopropyl | -NH-CH₂CH₂CH₂-OH | 3-((2-((5-cyclopropyl-1H-pyrazol-3-yl)amino)pyrrolo[2,1-f][1,2,4]triazin-4-yl)amino)-1-propanol | 314.35 | 2.127$^b$ |
| 27 | cyclopropyl | -NH-CH₂-CH(OH)-CH₃ (2S) | (2S)-1-((2-((5-cyclopropyl-1H-pyrazol-3-yl)amino)pyrrolo[2,1-f][1,2,4]triazin-4-yl)amino)-2-propanol | 314.39 | 2.412$^a$ |
| 28 | cyclopropyl | -NH-CH(CH₃)-CH₂OH (2S) | (2S)-2-((2-((5-cyclopropyl-1H-pyrazol-3-yl)amino)pyrrolo[2,1-f][1,2,4]triazin-4-yl)amino)-1-propanol | 314.38 | 2.192$^a$ |
| 29 | cyclopropyl | (2S)-tetrahydrofuran-2-ylmethyl-NH- | N²-(5-cyclopropyl-1H-pyrazol-3-yl)-N⁴-((2S)-tetrahydro-2-furanylmethyl)pyrrolo[2,1-f][1,2,4]triazine-2,4-diammine | 340.32 | 2.442$^a$ |
| 30 | cyclopropyl | 1-benzyl-3-pyrrolidinyl-NH- | N⁴-(1-benzyl-3-pyrrolidinyl)-N²-(5-mnethyl-1H-pyrazol-3-yl)pyrrolo[2,1-f][1,2,4]triazine-2,4-diamine | 389.38 | 2.042$^b$ |
| 31 | cyclopropyl | -NH-CH₂CH₂-S-CH₃ | N²-(5-cyclopropyl-1H-pyrazol-3-yl)-N⁴-(2-(methylsulfonayl)ethyl)pyrrolo[2,1-f][1,2,4]triazine-2,4-diamine | 330.23 | 2.543$^b$ |

TABLE 1-continued

| Ex. # | R¹ | R² | Compound name | [M + H] | HPLC Ret Time (min) |
|---|---|---|---|---|---|
| 32 | cyclopropyl | (1S)-1-cyclohexylethylamino | N⁴-((1S)-1-cyclohexylethyl)-N²-(5-cyclopropyl-1H-pyrazol-3-yl)pyrrolo[2,1-f][1,2,4]triazine-2,4-diamine | 366.30 | 3.323[b] |
| 33 | cyclopropyl | (2S)-2,3-dihydroxypropylamino | (2S)-3-((2-((5-cylopropyl-1H-pyrazol-3-yl)amino)pyrrolo[2,1-f][1,2,4]triazine-4-yl)amino)-1,2-propanediol | 330.25 | 1.967[a] |
| 34 | cyclopropyl | trans-4-hydroxycyclohexylamino | trans-4-((2-((5-cyclopropyl-1H-pyrazol-3-yl)amino)pyrrolo[2,1-f][1,2,4]triazin-4-yl)amino)cyclohexanol | 354.3 | 2.365[b] |
| 35 | cyclopropyl | ((2R)-tetrahydro-2-furanylmethyl)amino | N²-(5-cyclopropyl-1H-pyrazol-3-yl)-N⁴-((2R)-tetrahydro-2-furanylmethyl)pyrrolo[2,1-f][1,2,4]triazine-2,4-diamine | 340.27 | 2.442[b] |
| 36 | cyclopropyl | 2-hydroxybutylamino | 1-((2-((5-cyclopropyl-1H-pyrazol-3-yl)amino)pyrrolo[2,1-f][1,2,4]triazin-4-yl)amino)-2-butanol | 328.26 | 2.357[a] |
| 37 | cyclopropyl | (3R)-3-pyrrolidinylamino | N²-(5-cyclopropyl-1H-pyrazol-3-yl)-N⁴-((3R)-3-pyrrolidinyl)pyrrolo[2,1-f][1,2,4]triazine-2,4-diamine | 325.30 | 1.683[a] |

TABLE 1-continued

[Structure: R² group attached to pyrrolo[2,1-f][1,2,4]triazine core with NH linkage to pyrazole bearing R¹]

| Ex. # | R¹ | R² | Compound name | [M + H] | HPLC Ret Time (min) |
|---|---|---|---|---|---|
| 38 | cyclopropyl | (3S)-3-pyrrolidinyl (NH, HN-) | N²-(5-cyclopropyl-1H-pyrazol-3-yl)-N⁴-((3S)-3-pyrrolidinyl)pyrrolo[2,1-f][1,2,4]triazine-2,4-diamine | 325.28 | 1.697[b] |
| 39 | cyclopropyl | (1R)-1-(4-fluorophenyl)ethyl | N4-(3-cyclopropyl-1H-pyrazol-5-yl)-N2-((1R)-1-(4-fluorophenyl)ethyl)pyrrolo[2,1-f][1,2,4]triazine-2,4-diamine | 378 | 2.985b |
| 40 | cyclopropyl | (1S)-1-phenylethyl | N4-(3-cyclopropyl-1H-pyrazol-5-yl)-N2-((1S)-1-phenylethyl)pyrrolo[2,1-f][1,2,4]triazine-2,4-diamine | 360 | 2.93b |
| 41 | cyclopropyl | (1R)-1-phenylethyl | N4-(3-cyclopropyl-1H-pyrazol-5-yl)-N2-((1R)-1-phenylethyl)pyrrolo[2,1-f][1,2,4]triazine-2,4-diamine | 360 | 2.93b |

HPLC Conditions:
[a]YMC S5 Combiscreen ODS 4.6 × 50 mm, 10-90% aqueous methanol containing 0.2% H3PO4, 4 min gradient, monitored at 220 or 254 nm).
[b]Chromolith SpeedROD 4.6 × 50 mm, 10-90% aqueous methanol containing 0.1% TFA, 4 min gradient, monitored at 220 or 254 nm).
[c]Phenomenex Su C18 4.6 × 50 mm column 10-90% aqueous methanol containing 0.1% TFA, 4 min gard. monitored at 220 nm.

We claim:

1. A compound selected from the group consisting of
N²-(5-cyclopropyl-1H-pyrazol-3-yl)-N⁴-((1S)-1-(4-fluorophenyl)ethyl)pyrrolo[2,1-f][1,2,4]triazine-2,4-diamine
N²-(5-cyclopropyl-1H-pyrazol-3-yl)-N⁴-((1S)-1-methylpentyl)pyrrolo[2,1-f][1,2,4]triazine-2,4-diamine,
N⁴-(1-benzyl-3-pyrrolidinyl)-N²-(5-methyl-1H-pyrazol-3-yl)pyrrolo[2,1-f][1,2,4]triazine-2,4-diamine,
N⁴-(3-cyclopropyl-1H-pyrazol-5-yl)-N²-((1S)-1-phenylethyl)pyrrolo[2,1-f][1,2,4]triazine-2,4-diamine,
N⁴-(3-cyclopropyl-1H-pyrazol-5-yl)-N²-((1R)-1-phenylethyl)pyrrolo[2,1-f][1,2,4]triazine-2,4-diamine,
N⁴-((1S)-1-(4-fluorophenyl)ethyl)-N²-(5-methyl-1H-pyrazol-3-yl)pyrrolo[2,1-f][1,2,4]triazine-2,4-diamine,
N⁴-cycloheptyl-N²-(5-cyclopropyl-1H-pyrazol-3-yl)pyrrolo[2,1-f][1,2,4]triazine-2,4-diamine,
N⁴-(cyclohexylmethyl)-N²-(5-cyclopropyl-1H-pyrazol-3-yl)pyrrolo[2,1-f][1,2,4]triazine-2,4-diamine,
N⁴((1S)-1-cyclohexylethyl)-N²-(5-cyclopropyl-1H-pyrazol-3-yl)pyrrolo[2,1-f][1,2,4]triazine-2,4-diamine,
or a pharmaceutically acceptable salt or stereoisomer thereof.

2. A pharmaceutical composition comprising one or more compounds of claim 1 and a pharmaceutically acceptable carrier.

3. A pharmaceutical composition comprising one or more compounds according to claim 1 in combination with a pharmaceutically acceptable carrier and one or more other anticancer or cytotoxic agents.

4. A method for treating breast cancer comprising administering to a mammalian species in need thereof, a therapeutically effective amount of one or more compounds according to claim 1.

* * * * *